(12) United States Patent
Pauser et al.

(10) Patent No.: US 9,351,806 B2
(45) Date of Patent: May 31, 2016

(54) DEVICE FOR A DENTAL SUBSTANCE

(75) Inventors: Helmut Pauser, Diessen (DE); Marc Peuker, Schondorf (DE); Michael Knee, Peissenberg (DE); Werner Fichtl, Geltendork/Kallenberg (DE); Andreas Maurer, Langenneufnach (DE)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 0 days.

(21) Appl. No.: 13/322,269

(22) PCT Filed: May 21, 2010

(86) PCT No.: PCT/US2010/035703
§ 371 (c)(1),
(2), (4) Date: Jan. 25, 2012

(87) PCT Pub. No.: WO2010/138396
PCT Pub. Date: Dec. 2, 2010

(65) Prior Publication Data
US 2012/0115103 A1    May 10, 2012

(30) Foreign Application Priority Data
May 29, 2009  (GB) .................................. 0909167.9

(51) Int. Cl.
*A61C 5/04* (2006.01)
*A61C 5/06* (2006.01)

(52) U.S. Cl.
CPC ..................................... *A61C 5/062* (2013.01)

(58) Field of Classification Search
CPC .... A61C 5/062; A61C 19/063; A61C 9/0026; A61C 5/066; B05C 17/00593; B05C 17/00509; B05C 17/00583; B05C 17/00543; A61M 5/178; A61M 2005/2492
USPC .............. 433/80, 89, 90, 97, 82–83; 401/181; 222/566–574, 326–327, 386–391; 604/187, 218–231
See application file for complete search history.

(56) References Cited

U.S. PATENT DOCUMENTS

| | | | | |
|---|---|---|---|---|
| 4,235,235 A | * | 11/1980 | Bekkering | A61M 5/3129 604/238 |
| 4,619,613 A | * | 10/1986 | Dragan | 433/90 |
| 5,122,057 A | | 6/1992 | Discko | |
| 5,129,825 A | | 7/1992 | Discko | |
| 6,877,983 B1 | * | 4/2005 | Dragan et al. | 433/90 |
| 2003/0075624 A1 | * | 4/2003 | Reisinger | 239/600 |
| 2003/0186191 A1 | * | 10/2003 | Lawter et al. | 433/90 |

(Continued)

FOREIGN PATENT DOCUMENTS

WO   WO 2009/151983   12/2009

OTHER PUBLICATIONS

Adjacent. (n.d.). Dictionary.com Unabridged. Retrieved Mar. 18, 2015, from Dictionary.com website: http://dictionary.reference.com/browse/adjacent.*

(Continued)

*Primary Examiner* — Heidi M Eide
(74) *Attorney, Agent, or Firm* — Nicole J. Einerson (57) ABSTRACT

A dispensing device for a dental substance which has a container for receiving the dental substance, a piston movable in the container, a catch for engagement by an applicator, and further a resilient resilient adapter. The device may be used in different types of applicators and is relatively inexpensive.

19 Claims, 3 Drawing Sheets

(56) References Cited

U.S. PATENT DOCUMENTS

2007/0164047 A1    7/2007   Reidt
2007/0228076 A1   10/2007   Horner
2008/0071226 A1*   3/2008   Moser et al. .................. 604/207
2009/0142728 A1*   6/2009   Lawter et al. ................... 433/89

OTHER PUBLICATIONS

International Search Report for International Application No. PCT/US2010/035703, dated Aug. 20, 2010.

* cited by examiner

DEVICE FOR A DENTAL SUBSTANCE

CROSS REFERENCE TO RELATED APPLICATIONS

This application is a national stage filing under 35 U.S.C. 371 of PCT/US2010/035703, filed May 21, 2010, which claims priority to Great Britain Patent Application No. 0909167.9, filed May 29, 2009, the disclosures of which are incorporated by reference in their entirety herein.

FIELD OF THE INVENTION

The invention relates to a dispensing device for a dental substance, and in particular to a dispensing device which may be used with an applicator.

BACKGROUND ART

Dental substances are often provided in devices allowing the substance to be dispensed directly to a desired location, for example on a dental pad or in a patient's mouth. Such dispensing devices typically have a chamber for holding the dental substance, an outlet, and a piston for extruding the substance from the chamber through the outlet.

A variety of dispensing devices are designed for dispensation of relatively high viscosity dental substances, like for example dental filling materials. Some of those dispensing devices are configured for use with an applicator providing an extrusion force that is sufficient for dispensation of high viscosity dental substances. In dentistry several types of manually operated applicators are available which provide leverage for increasing manual forces to provide sufficient extrusion forces. Many applicators are designed as a reusable tool which forms part of a dental practice's basic equipment.

Although a variety of applicators and dispensing devices are available there is a desire to provide a dispensing device which can be used with applicators already available in the market. Further it is desirable to provide a dispensing device which is easy to use in combination with such applicators, and which is further relatively inexpensive.

SUMMARY OF THE INVENTION

One aspect of the invention relates to a dispensing device for a dental substance. The device comprises a back end and, further to the front, a dispensing end. Further the device comprises a container for receiving the dental substance, and a piston movable in the container along an extrusion path for extruding the dental substance, for example from the container, toward the dispensing end. The device also comprises a catch extending laterally to the extrusion path, and a resilient adapter. The catch is adapted to restrain or to catch the device, for example in an applicator, in a direction generally parallel to the extrusion path, and the resilient adapter is resilient in at least a direction perpendicular to the extrusion path.

The invention is advantageous in that it may enable the use of the dispensing device with different applicators, for example different applicators of the same or a different type. The invention may further be advantageous in that it may facilitate coupling of the dispensing device with an applicator by a user. The features of the invention may for example allow for preliminary positioning of the device in the applicator before the device is finally locked into the applicator. The invention may further allow a relatively precise and sustainable adjustment of the device in the applicator, and may thus be advantageous in use to dispense a dental substance precisely to a desired location, for example in a patient's mouth. Therefore the invention may generally facilitate handling of the device. Furthermore the invention may allow for relatively inexpensive manufacturing of such a dispensing device.

In one embodiment the catch is adapted to retain or lock the device in an applicator, for example against a force applied to extrude the dental substance. Such an applied extrusion force may further be oriented in a direction parallel, or substantially parallel, to the extrusion path. The catch may for example be sufficiently stable and sufficiently well connected to the container such that it can support the device against a resulting force of at least about 300 N. This preferably allows the device to be used with an applicator that provides leverage sufficient to convert a manual force to a higher extrusion force.

The extrusion path is preferably substantially straight. The extrusion path may further be substantially circular. Preferably the extrusion path has a generally constant curvature or may be generally zero.

In one embodiment the catch is formed by a continuous annular rim around the container. Therefore if the container is for example essentially cylindrical the catch may be ring-shaped. The catch may extend annularly with a generally rectangular cross-section. The catch may therefore form a generally cylindrical ring. However the catch may also extend annularly with a generally triangular or trapezoidal cross-section. In that case the catch may be conical. A conical catch preferably has a larger diameter toward the dispensing end. This may help for the device to be securely retained in an applicator.

Generally the catch may protrude laterally from the container. In particular the catch may extend laterally from the outer container surface. The catch in combination with the outer container surface may therefore provide the device with a step which is positively engageable to hold the device in an applicator, for example. The skilled person will understand that there are other configurations that provide a catch. The catch may be formed, for example, by a notched annular rim, or by one or more retention elements in the form of pins, webs, or fins for example. In one example a plurality of webs may be arranged annularly around the container and protrude from the outer container surface. Such webs may have a dimension generally along or generally parallel to the extrusion path (or a tangent of the extrusion path), and protrude radially relative to the extrusion path (or a tangent of the extrusion path).

In a preferred embodiment the catch is arranged adjacent or at the back end of the device.

The resilient adapter may provide the device at least partially with a variable lateral or radial dimension. This can be useful because different applicators may have differently sized receptacles for receiving devices. The resilient adapter may thus allow the device to exhibit or adapt to different lateral dimensions that may be required to enable an applicator to dispense material from the device. Therefore the resilient adapter may allow the device to be received in different applicators or different types of applicators. Further the resilient adapter may allow the device to be laterally restrained within an applicator. The person skilled in the art may therefore regard the resilient adaptor also as spring adapter, clamp adapter or size compensation adapter.

In one embodiment the resilient adapter is formed by a continuous annular rim around the container. For example if the container is cylindrical the resilient adapter may form a ring shaped rim. The annular rim may further be notched. The resilient adapter is preferably connected to the device with a first end of the resilient adapter. The resilient adapter preferably further has a free second end. The resilient adapter is preferably adapted (for example dimensioned and/or made from a certain material) such that at least the second end of the rim is resilient.

The resilient adapter may extend annularly with a cross-section formed of an elongated dimension and a reduced dimension transverse to the elongated dimension. Therefore the resilient adapter may have a generally rectangular, a generally triangular or a generally trapezoidal cross-section which extends annularly. Preferably the elongated dimension extends in a direction generally from the first to the second end of the resilient adapter. The elongated dimension relative to the reduced dimension may be in a ratio between about 2 and about 10, preferably about 5. Therefore an appropriate resilience of the resilient adapter may be achieved.

In another embodiment the elongated dimension of the cross-section is oriented in a direction substantially parallel to or inclined relative to the extrusion path. For example the resilient adapter may form a generally cylindrical or funnel-shaped tube. A funnel shaped resilient adapter preferably is wider toward the back end of the device. The resilient adapter may at least have an outer surface which is inclined with respect to the extrusion path. For example the outer surface of the resilient adapter in a direction from the dispensing end towards the back end of the device may be sloped away from the extrusion path. The resilient adapter when placed in a receptacle of an applicator may be compressed such that the resilient adapter adopts the dimension of the receptacle, for example. A device having a funnel-shaped or inclined resilient adapter may be particularly advantageous when placed in a generally cylindrical receptacle of an applicator, for example.

The resilient adapter rim may protrude from the catch in a direction substantially parallel to the extrusion path. For example the resilient adapter may be connected to the catch and extend with its elongated dimension away from the catch. The resilient adapter may for example protrude backwardly from the catch. For example the resilient adapter may be connected to the catch at a surface facing to the back end of the device.

Thus the catch and the resilient adapter in combination may extend annularly with a generally L-shaped cross-section. The L-shaped cross-section may be oriented with one leg (for example belonging to the catch) connected to and extending perpendicularly from the device and the other leg (for example belonging to the resilient adapter) extending toward the back end of the device. The resilient adapter may thus surround the container with a free space between.

The resilient adapter may further protrude (for example backwards) over the back end of the container. Accordingly the resilient adapter may surround a virtual elongation of the container in a direction along the extrusion path.

The resilient adapter may further protrude laterally from the catch. For example the resilient adapter may be connected to the catch at a surface extending radially relative to the extrusion path.

In one embodiment the catch and the resilient adapter may form one piece with one another.

In a further embodiment the resilient adapter protrudes laterally from the container. The resilient adapter may be arranged between the catch and the back end of the container. The resilient adapter may further be arranged between the catch and the dispensing end of the device. The resilient adapter may particularly be spaced from the catch. One or multiple such resilient adapters may be arranged on the container. The catch and the resilient adapter(s) may be formed in one piece (unitarily) with the container.

In one embodiment the catch has a lateral first dimension with respect to the extrusion path (for example an outer catch diameter), and the resilient adapter has a lateral second dimension with respect to the extrusion path (for example an outer resilient adapter diameter), wherein the second dimension is greater than the first dimension. Therefore the catch may loosely fit in an applicator, but the resilient adapter may fit more tightly therein. Thus the device may be preliminarily retained or clamped in an applicator without, or before, locking the catch therein.

The resilient adapter may be laterally more resilient than the catch. In particular the resilient adapter may be more resilient in a direction perpendicular to the extrusion path than the catch in a direction parallel to the extrusion path. The resilient adapter may further be more resilient in a direction generally perpendicular to the extrusion path than in a direction generally parallel to the extrusion path. The resilience of the resilient adapter perpendicular to the extrusion path may be generally provided by structure (for example by the shape of the resilient adapter). For example the structure of the resilient adapter may comprise portions having a wall thickness that is smaller than the minimum wall thickness of the catch. Further the resilient adapter may have different wall thicknesses in different dimensions, for example a smaller wall thickness generally perpendicular to the extrusion path and a greater wall thickness generally parallel to the extrusion path. The wall thickness of the resilient adapter in one dimension preferably enables the resilient adapter to deflect in that dimension under load, with the same load being insufficient to deflect the catch and/or the resilient adapter in at least one further dimension (for example in a dimension generally along the extrusion path).

The resilience of the resilient adapter perpendicular to the extrusion path may further be provided by material (for example by the natural resilience of the material the resilient adapter is made of). The material may enable the resilient adapter to be compressed under load. The skilled person may recognize other configurations, for example the use of a more resilient material (for example rubber) for the resilient adapter relative to the material used for the catch, or a combination of resilience provided by structure and resilience provided by material.

In one embodiment the device has a cannula for dispensing the dental substance from the dispensing end. The device may further be adapted to receive a cannula adjacent the dispensing end for dispensing the dental substance. For example the device may have a coupling end for mating with a corresponding coupling end of a cannula. The dispensing end (either as part of the cannula or the device) may particularly be formed by an end of the cannula. The cannula may be sized and shaped such that the cannula can be used to apply dental substance into the gingival sulcus in a patient's mouth. The end of the cannula may for example convexly taper towards the end from a first diameter toward a smaller second diameter. The first diameter may for example be between about 0.6 mm and about 1.5 mm, and in particular the first diameter may be between about 0.9 and 1.4 mm. Preferably the first diameter is about 1.0 mm. The second diameter may be between about 0.2 mm and about 1.0 mm, and in more particular the second diameter may be between about 0.3 mm to 0.7 mm. The second diameter is preferably about 0.4 mm. The distance between the first and second diameters may be between about 0.6 mm and 1.5 mm, preferably about 1.0 mm. Further the length of the cannula may be between about 4.0 mm and 18.0 mm, in particular between about 6.0 and 14.0 mm, preferably about 11.0 mm. Furthermore the taper preferably tapers based on a curve having a relatively constant radius. The radius may be greater than ½ of the first diameter. For example, the shape of the free end may resemble a nose cone, a convex cone, or a radial cone. A curve resembling a radius greater than ½ of the second diameter may provide for a relatively low force required to insert the free end of the cannula in the entry of the gingival sulcus. An exemplary radius which the taper may be based on is about 3.0 mm.

A relatively small dimension of the second diameter may allow the end of the cannula to be inserted in the entry of the gingival sulcus of a patient relatively easily. The tapered shape may facilitate a smooth insertion into the sulcus because a sharp vertex at the cannula end may thus be avoided. Further the first diameter as specified may provide the cannula with a certain stiffness to avoid buckling when the cannula is pushed toward and into the sulcus. Therefore the device of the invention may be suitable to inject a dental substance in the gingival sulcus. A cannula as it may be used with the present invention is for example disclosed in co-pending European Patent Application No.: EP 08158033.4 which is incorporated by reference herein.

In another embodiment the cannula is arranged adjacent the container. In particular the cannula may be arranged at the container. For example the container and the cannula may be formed in one piece. The cannula may protrude from the container in an angle, for example an angle of between about 30 degrees and 60 degrees, and preferably about 42 degrees. An inclination of the cannula relative to the container may for example help maximizing the possibility of reaching different locations in a patient's mouth.

In a further embodiment the container extends between the back end of the device and the cannula. The container may for example with a first container end form the back end of the device. At a second container end the container may merge with the cannula. The container preferably has a lateral outer container surface extending along the extrusion path. The extrusion path may be generally linear. Accordingly the outer container surface may be cylindrical or generally cylindrical. Further the extrusion path may be curved, for example circularly curved. Accordingly the outer container surface may form a section of a torus. In the embodiment having a curved extrusion path the cannula may also be curved and extend along or parallel to an elongation of the extrusion path. Alternatively the cannula may be generally straight, and extend along (or parallel to a tangent of) the extrusion path. Therefore the cannula, or a tangent of the cannula, may be inclined with respect to a tangent of the extrusion path adjacent the device back end at angles as mentioned above. This may also help maximizing the possibility of reaching different locations in a patient's mouth.

The skilled person will understand that the container may have one chamber for storing the dental substance or multiple chambers for storing components of a dental substance. Such components may for example be mixed when the components are extruded from the device, for example in a mixer that is connected to the device. Further multiple chambers may be arranged concentrically and/or side by side.

The outer container surface may have a diameter of between about 5 mm and about 8 mm, preferably about 6.5 mm.

In one embodiment the dispensing device is used or combined with an applicator. The applicator may have a receptacle for receiving at least the back end of the device. The receptacle may comprise first and second portions. The first and second portions may in combination form a stop for engaging the catch. Thus the receptacle may comprise a stop for engaging the catch. The stop may be formed by a step between the first portion of the receptacle and the second portion of the receptacle which is widened relative to the first portion. The container is preferably sized and shaped to fit in the first portion of the receptacle. Further the catch is preferably sized and shaped to fit in the second portion of the receptacle but not in the first portion. Thus the catch can positively engage with the stop of the applicator.

The resilient adapter may be sized and shaped to form a force-fit with a second portion of the receptacle. The resilient adapter may clamp within the second portion of the receptacle. Therefore when the resilient adapter is received in the receptacle the device may be releasably retained in the device, for example for preliminary positioning within the applicator before the device is finally locked into the applicator. Further the device may be rotatable but, because of the clamping effect, reliably retained in a certain rotational position. This may facilitate handling of the device during treatment of a patient for example.

In another embodiment the applicator has a third portion which is widened relative to the second portion. The resilient adapter may be sized and shaped to loosely fit within the third portion of the receptacle. This may allow the device to be inserted in the receptacle relatively easily.

The device may be receivable in the receptacle in a first position and movable in a direction generally along the extrusion path toward a second position. In the first position the resilient adapter may be mated with the third portion of the receptacle, whereas in the second position the resilient adapter may be mated with the second portion of the receptacle. Further in the first position the catch may be positioned spaced from the stop, whereas in the second position the catch abuts the stop. The container may be guided by the first portion in the first and/or the second position.

In a further embodiment the applicator comprises a handle and a plunger. The handle may be adapted for manual operation and for advancing the plunger. The plunger may be adapted to extend into the device to advance the piston along the extrusion path for extruding dental substance from the device.

DETAILED DESCRIPTION OF THE INVENTION

Figure 1:
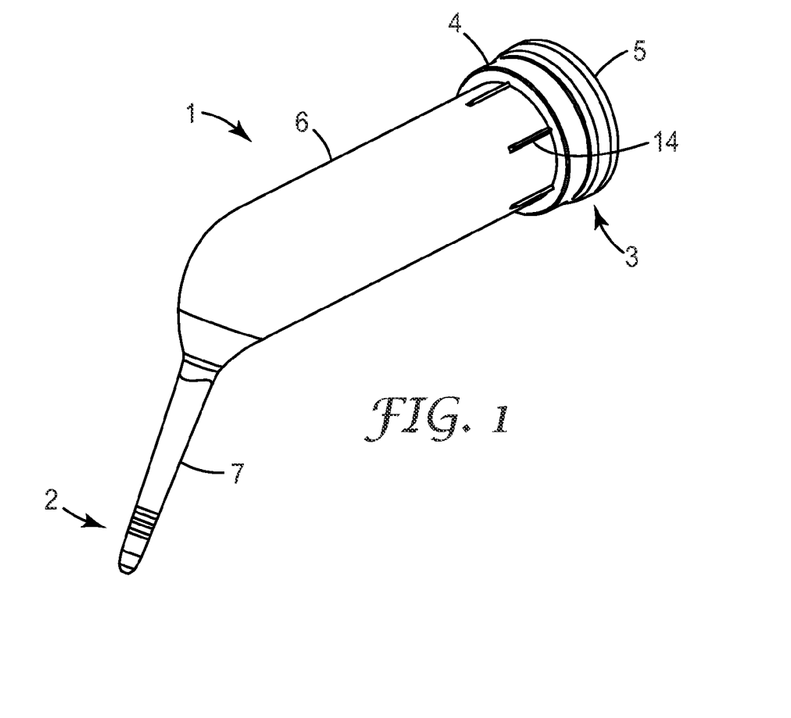
FIG. 1 is a perspective view of a device according to an embodiment of the invention.
Figure 5:
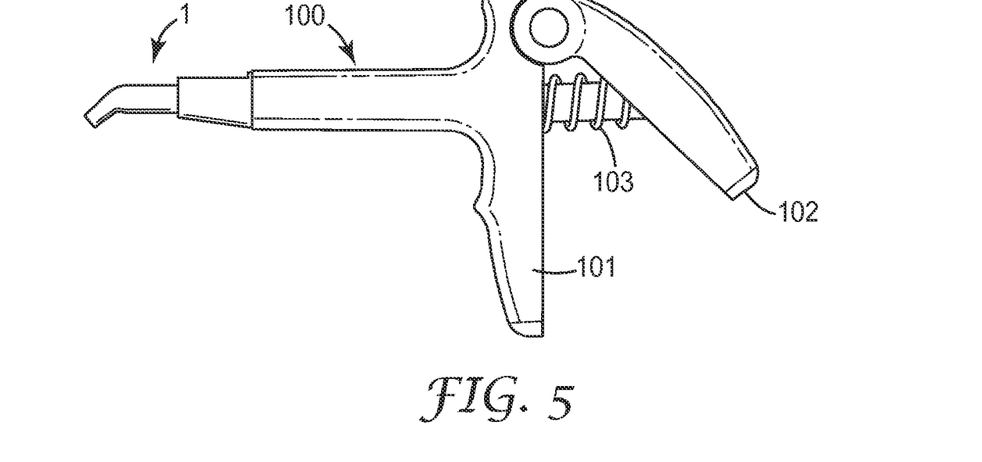
FIG. 5 is a side view of a device in combination with an applicator according to an embodiment of the invention.

FIG. 1 shows a device 1 for containing a dental substance. The device 1 may for example be used to dispense the dental substance to a desired location in a patient's mouth. The device 1 has a dispensing end 2 from which the dental substance may be dispensed and a back end 3 which is configured to use the device 1 with an applicator. In particular the back end 3 comprises a catch 4 and a resilient adapter 5 allowing the device 1 to be retained or locked in the applicator. Such an applicator (an example is shown in FIG. 5) may facilitate dispensing of the dental substance from the dispensing end.

The device 1 has further a container 6 and may have a cannula 7. The container 6 in the illustrated example extends generally linearly and the cannula 7 extends at an angle therefrom. This configuration may for example facilitate reaching certain places in a patient's mouth with the cannula during a dental treatment. The skilled person may however appreciate other configurations, for example configurations in which the cannula and the container are co-aligned or parallel with one another. Further the container 6 may extend along a curve, for example a circular or generally circular curve. In this example the cannula may be co-aligned with the curve the container extends along. Thus a configuration is provided which may be likewise suitable to reach certain locations in a patient's mouth more effectively than with a straight device and cannula. The device 1 further has a plurality of ribs 14 each radially outwardly protruding from an outer surface of the container 6. The ribs 14 in the example are substantially uniformly distributed around the container and extend substantially linearly in a general direction between the back end 3 and the dispensing end 2. The ribs 14 are further connected with the catch 4 and have a free edge in a direction toward the dispensing end 2. Thus the ribs 14 are relatively rigid adjacent the catch and softer in a direction away from the catch 4. The ribs 14 may be used to support and/or guide the device 1 in an applicator. For example the device may be placed with the ribs with the free edges leading and the catch trailing into a recess of the applicator. The ribs positioned only partially in the recess may provide for a slight retention whereas the ribs positioned further within the recess may provide a tighter retention. Thus the retention of the device 1 in the application may be user adjustable. This may also be advantageous for example for adjusting a desired rotational retention of the device in the applicator which on the one hand still allows the device to be rotated, but prevents the device from unintentional rotation during use in a treatment of the patient.

Figure 2:
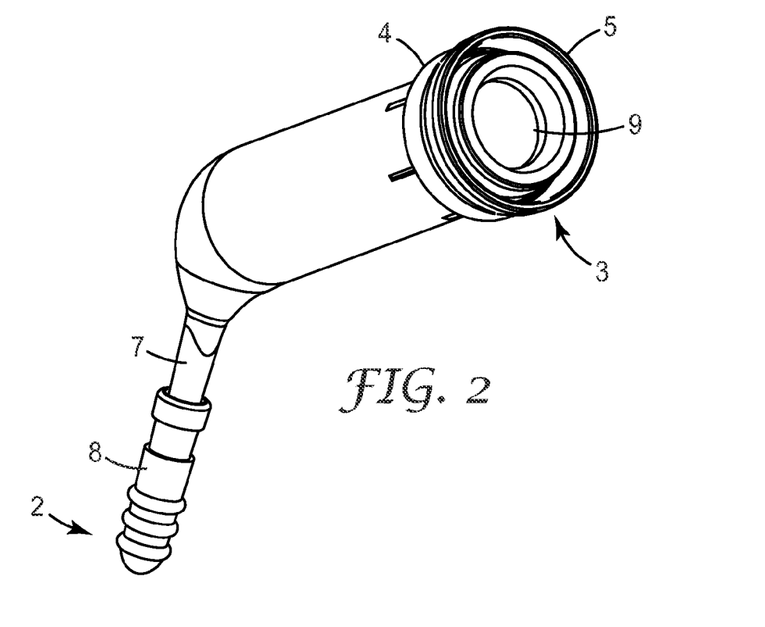
FIG. 2 is a perspective view showing some details of a device according to an embodiment of the invention.

FIG. 2 shows the device 1 from a different perspective. The device 1 in this example comprises a cap 8 which seals the device 1 at the dispensing end 2. The cap 8 is preferably receivable on the cannula 7 to hermetically seal the device 1 at the dispensing end 2. Further the device 1 is sealed by a piston 9 at the back end 3. The piston 9 is preferably receivable in a chamber (not visible in FIG. 2) of the device 1 that holds the dental substance, and is preferably movable in the chamber to urge the dental substance toward the dispensing end 2. The piston 9 preferably also seals the device hermetically. Therefore the configuration shown in the example may allow a dental substance to be stored in the device 1 over a relatively long time, for example three, six, or more months, and thereby sufficiently protecting the dental substance from the environment so that it still can be used after a storage time as mentioned.

Figure 3:
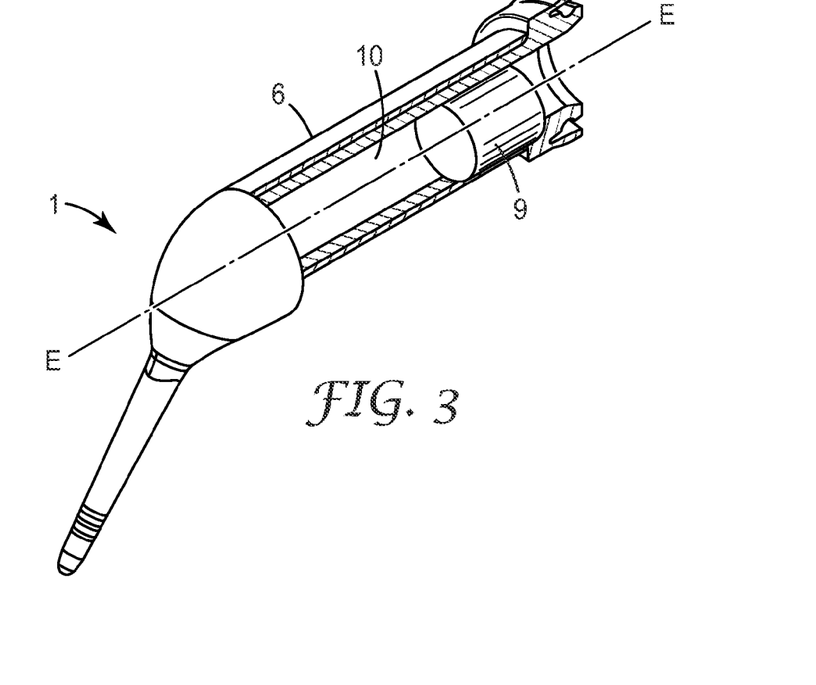
FIG. 3 is a partial cross-sectional view of a device according to an embodiment of the invention.

FIG. 3 is a partial cross-sectional view of the device 1 showing the chamber 10 which may receive the dental substance. Piston 9 is received in the chamber. The container 6 of the device 1 in the example has a generally ring shaped circular cross-section. Therefore the outer surface of the container 6 is at least partially generally cylindrical. And further also the inner surface of the container 6, which forms a surface of the chamber 10 is at least partially generally cylindrical. Other configurations are possible as mentioned above. For example the ring shaped cross-section may extend along a generally circular curve, rather than along a straight as shown. Further the ring shape may comprise an inner and/or an outer elliptical shape, or any other suitable shape like triangular, rectangular, or hexagonal shapes for example.

Thus the container 6 may be shaped to match the receptacle of an applicator, for example to fit loosely in the receptacle of the applicator. The path the chamber 10 extends along forms the extrusion path E-E which is the path along which the piston is advanced to extrude substance from the device. The extrusion path E-E in this example is linear.

Figure 4:
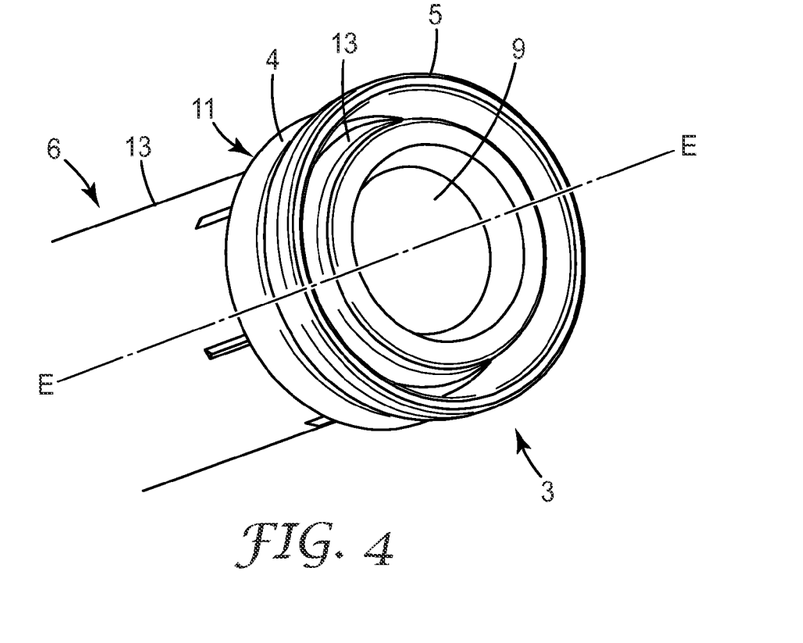
FIG. 4 is a perspective view of a back end of a device according to an embodiment of the invention.

FIG. 4 shows in detail the back end 3 of the device according to an embodiment of the invention. The catch 4 is preferably adapted to prevent movement due to forces in a direction of the extrusion path E-E. In particular the catch 4 may be adapted to retain the device 1 against forces that are exerted on the piston 9 for extrusion of the substance. The catch 4 in the example is arranged as an annular rim around a section of the container 6. In particular the catch 4 may be a generally solid rim which is preferably formed in one piece with the container. Other configurations are possible. For example the annular rim may be notched in one or more locations. Further, instead of a rim, at least one individual retention member that protrudes from the outer surface of the container 6 may be used as a catch. In another embodiment the catch may be formed by a rim which is supported by webs that connect the outer surface of the container and a rear face (facing toward the back end of the device) of the rim. The catch may in any embodiment have a front face 11 which extends generally transverse or radially away from the outer surface of the container 6. Therefore the catch may form a step on the container 6. This may help securely retaining the device in the applicator. The back end 3 further has a resilient adapter 5. In the example the resilient adapter 5 protrudes from a rear face, which is the face opposite of the front face 11, of the rim backwards. The resilient adapter 5 is generally ring-shaped. Preferably the resilient adapter is formed in one piece with the catch. However the resilient adapter because of its dimensions and arrangement relative to the container is preferably more compressible and resilient. However the resilient adapter may also be separately formed, for example formed from a material other than the catch. The resilient adapter 5 may be used for laterally positioning the capsule in the applicator as described below in more detail.

Figure 6:
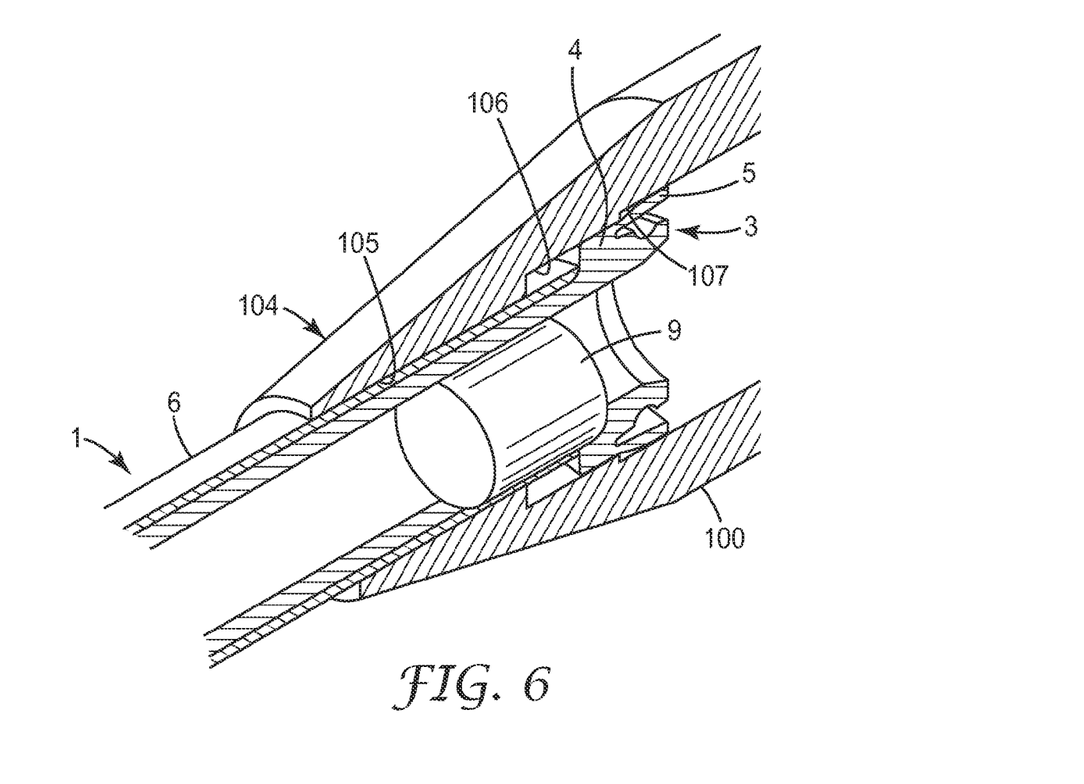
FIG. 6 is a perspective cross-sectional view of a back end of a device when received in an applicator according to an embodiment of the invention.

FIGS. 5 and 6 show the device 1 in cooperation with the applicator 100. The applicator shown is for example available from 3M ESPE AG, Germany under the designation Capsule Dispenser. The applicator has a pair of handles 101, 102 and a plunger 103 that can be advanced against spring load by the handle 102. The plunger can extend into the device 1 to advance the piston of the device 1 while the device is retained in the applicator. The extrusion forces may be about 50 N to 300 N, in particular about 140 N. Therefore the handles 101, 102 of the applicator provide for leverage which increases manual forces to produce sufficient extrusion forces, thus facilitating dispensation of the substance from the device.

FIG. 6 shows in more detail the cooperation between the back end 3 of the device 1 and the applicator 100. Shown is a mouth portion 104 of the applicator 100. The mouth portion 104 has a receptacle 105 which is adapted to receive the back end 3 of the device 1. The receptacle may have a hole or a groove in which the back end 3 of the device can be placed. The receptacle 105 has a first widened portion 106 which provides a step in the receptacle 105. In the example the step forms a catch which is adapted to engage the catch 4 of the device. The skilled person will recognize other configurations for forming a catch in the device, for example jaws, pawls or clutches. Preferably once the device 1 is placed in the applicator the device is retained or locked by the catch with respect to forces exerted on the device in the direction from the back end toward the dispensing end, for example in the direction of the extrusion path. Thus the plunger 9 may be advanced in the direction toward the dispensing end while the device is held back by the catch at the catch 4, thereby dispensing the material.

The container 6 of the device 1 is adapted to fit into the receptacle 105, and the catch 4 of the device 1 is adapted to fit into the first widened portion 106 of the receptacle 105. The container 6 and the catch 4 are preferably shaped and sized to fit within the receptacle 105. In particular the container 6 and the catch 4 are preferably shaped and sized so that they loosely fit with the receptacle 105. This may facilitate insertion of the device in the applicator by a user. The resilient adapter 5 is preferably oversized with respect to the receptacle 105, in particular in the example relative to the first widened portion 106 of the receptacle 105. Therefore the resilient adapter 5 is adapted to clamp in the mouth portion 104 of the applicator 100, particularly in the receptacle 105. The outer dimension (in the example diameter) of the catch 4 is preferably smaller than the outer dimension (in the example diameter) of the resilient adapter 5. The resilient adapter 5 preferably has a dimension (diameter) of between about 8.0 mm and about 9.0 mm between, preferably about 8.5 mm. The catch 4 preferably has a dimension (diameter) of between about 7.0 mm and about 8.5 mm between, preferably about 8.0 mm.

The receptacle 105 may have a second widened potion 107 which is also widened with respect to the first widened portion 106. The resilient adapter 5 may be shaped and sized so that it loosely fits with the second widened portion 107 of the receptacle 105. Thus the device 1 may be inserted in the mouth portion 104 of the applicator 100 such that the resilient adapter 5 is initially placed in the second widened portion 107. The device 1 may subsequently be moved toward the dispensing end to move the resilient adapter 105 into the first widened portion 106. Therefore insertion of the device 1 in the applicator may be facilitated. On the other hand the device 1 may also be clamped in the device so that it is prevented from falling off during handling of the applicator prior to use of the device. The clamping may also be advantageous in that it slightly retains the device against rotation in the device. A user may therefore be enabled to adjust the orientation of the cannula of the device relatively precisely and permanently.

A receptacle 105 of a suitable applier may have a dimension or diameter of between about 6.5 mm and about 7.0 mm, preferably about 6.5 mm. The first widened portion may have a dimension or diameter of between about 8.0 mm and about 9.0 mm, preferably about 8.1 mm.

The resilient adapter 5 may be formed, as shown, as a relatively thin walled ring which is spaced from the outer surface 13 of the container. Therefore the resilient adapter 5 in the example is resiliently deflectable into the space between the resilient adapter and the outer surface 13 of the container 6. The relatively thin wall in a direction generally perpendicular to the extrusion path provides the resilient adapter 5 with certain elasticity in that direction. In contrast the catch 4 has a wall which is thicker in a direction generally parallel to the extrusion path than the thin wall of the resilient adapter. Therefore the resilient adapter 5 is more resilient in a direction generally perpendicular to the extrusion path than the catch in a direction generally parallel to the extrusion path. In the example, the catch 4 further has a wall that is thicker in a direction generally perpendicular to the extrusion path than the thin wall of the resilient adapter and therefore is also less resilient than the resilient adapter in the same direction.

Other embodiments are possible. For example the resilient adapter 5 may be made from a material that is more elastic than the catch 4. In this case a space may not be required because the material as such may be compressible. In the example the resilient adapter 5 surrounds the outer surface 13 of the container 6. However the container 6 may only extend up to the catch 4, for example up to the rear face of the rim. In this case the resilient adapter 5 would protrude over the rear end of the container 6.

The catch 4 may be more rigid (less deformable) than the resilient adapter so that it is sufficiently stable even when relatively high forces are applied in the direction of the extrusion path.

The resilient adapter 5 is preferably sufficiently resilient so that it is compressible to compensate for about between 2% and 10%, and preferably about 6% relative to its outer dimension. For example a resilient adapter having an initial diameter of about 8.5 mm may be compressible down to a compressed diameter of about 8.0 mm. Therefore the device of the invention may provide for compensating tolerances of the receptacle of the applicator and still provide the clamping function. In particular the device may thus provide the clamping function in a variety of applicators or different types or brands of applicators.

The resilient adapter may be inserted in the first widened portion 106 generally radially or axially. For radial insertion the first widened portion 106 may have a lateral opening, for example having an opening width corresponding to the lateral dimension of the first widened portion 106. The force required for insertion is preferably below 10 N. Thus a convenient insertion of the device into the applier is achieved. The insertion force of below 10 N is preferably also sufficient to provide for a compression of the resilient adapter of about between 2% and 10%, and preferably about 6% relative to its outer dimension.

The invention has now been described by way of example only. The skilled person may appreciate other embodiments providing similar or equivalent functions. In particular the resilient adapter may be formed in a variety of configurations. For example the resilient adapter may be formed as a relatively thin lip which annularly protrudes from the outer surface of the container of the device. The resilient adapter may further by arranged rearwards (in a direction from the dispensing end toward the back end) or forwards (in the opposite direction) relative to the catch, adjacent the catch, abutting the catch or spaced from the catch, as well as combinations thereof.

The container, the catch and the resilient adapter may be made from a plastic material selected from among Polybutylene Terephthalate, Acrylonitrile-Butadiene-Styrene Terpolymer, Polycarbonate, and Polyoxymethylene.

The piston may be made from plastic materials selected from among Polyethylene, Polypropylene, Styrene Acrylonitrile Copolymer, polytetrafluoroethylene, and Polybutylene Terephthalate. Other materials are possible as appropriate.

Dental materials as they may be used with the present invention include, for example, dental impression materials, dental sealants, materials for dental prophylaxis, dental glass ionomers, dental etching gels, dental adhesives, dental restorative composite, dental temporary filling materials, dental composites for temporary restoration, dental cements (for example veneer cements), and dental refraction materials.

The invention claimed is:
1. A dispensing device for a dental substance, comprising:
   a container for receiving the dental substance, the container having a dispensing end and a back end;
   a piston movable in the container along an extrusion path for advancing the dental substance toward the dispensing end;
   a catch extending in a direction lateral to the extrusion path and dimensioned to be received in a receptacle of an applicator to restrain the device against movement, relative to the applicator, in a direction generally parallel to the extrusion path, wherein the catch is adjacent to the back end of the dispensing device or at the back end of the dispensing device; and a resilient adapter, wherein the resilient adapter is resilient in a direction perpendicular to the extrusion path, wherein the resilient adapter comprises a continuous annular rim around the container, and wherein the resilient adapter comprises portions having a wall thickness smaller than a minimum wall thickness of the catch so that the resilient adapter is laterally more resilient than the catch, wherein an inner surface of the resilient adapter is spaced from an outer surface of the container.

2. The dispensing device of claim 1, wherein the catch is formed by a continuous or notched annular rim around the container.

3. The dispensing device of claim 1, wherein the catch protrudes laterally from the container.

4. The dispensing device of claim 1, wherein the resilient adapter protrudes from the catch in a direction substantially parallel to the extrusion path.

5. The dispensing device of claim 4, wherein the resilient adapter protrudes backwardly from the catch.

6. The dispensing device of claim 1, wherein the resilient adapter surrounds the container with a free space between.

7. The dispensing device of claim 1, wherein the catch and the resilient adapter in combination extend annularly with a generally L-shaped cross-section.

8. The dispensing device of claim 1, wherein the catch and the resilient adapter are formed in one piece with one another.

9. The dispensing device of claim 1, wherein the resilient adapter protrudes laterally from the container.

10. The dispensing device of claim 9, wherein the catch is adjacent to the back end of the device and the resilient adapter is arranged between the catch and the back end of the device.

11. The dispensing device of claim 1, wherein the catch and the resilient adapter are formed in one piece with the container.

12. The dispensing device of claim 1, wherein the catch has an outer lateral first dimension with respect to the extrusion path, and the resilient adapter has an outer lateral second dimension with respect to the extrusion path, wherein the outer lateral second dimension is greater than the outer lateral first dimension.

13. The dispensing device of claim 1, wherein the device further comprises a cannula adjacent the dispensing end for dispensing the dental substance.

14. The dispensing device of claim 1, wherein the resilient adapter protrudes further laterally outwardly with respect to the container than the catch.

15. The dispensing device of claim 1, wherein the resilient adapter is deflectable into the space between the resilient adapter and the outer surface of the container.

16. A dispensing device in combination with an applicator, the dispensing device comprising:
a container for receiving the dental substance, the container having a dispensing end and a back end,
a piston movable in the container along an extrusion path for advancing the dental substance toward the dispensing end,
a catch extending in a direction lateral to the extrusion path and adapted to restrain the device against movement in a direction generally parallel to the extrusion path, wherein the catch is adjacent to the back end of the dispensing device or at the back end of the dispensing device, and
a resilient adapter, wherein the resilient adapter is resilient in a direction perpendicular to the extrusion path and wherein the resilient adapter comprises a continuous annular rim around the container; and
the applicator comprising:
a receptacle for receiving at least the back end of the device, the receptacle comprising first and second portions, wherein the second portion is widened relative to the first portion,
a third portion of the receptacle which is widened relative to the second portion, and
a catch for engaging the catch of the dispensing device, the catch of the applicator being formed by a step that is formed between the first and second portions of the receptacle.

17. The dispensing device of claim 16, wherein the container is sized and shaped to fit in the first portion of the receptacle, and the catch of the device is sized and shaped to fit in the second portion of the receptacle but not in the first portion, so that the catch of the device can positively engage with the catch of the applicator, and wherein the resilient adapter is sized and shaped to form a force-fit with the second portion of the receptacle, and wherein the resilient adapter is sized and shaped to loosely fit within the third portion of the receptacle.

18. A dispensing device for a dental substance, comprising:
a container for receiving the dental substance, the container having a dispensing end and a back end;
a piston movable in the container along an extrusion path for advancing the dental substance toward the dispensing end;
a catch extending in a direction lateral to the extrusion path and adapted to restrain the device against movement in a direction generally parallel to the extrusion path, wherein the catch is adjacent to the back end of the dispensing device or at the back end of the dispensing device; and
a resilient adapter, wherein the resilient adapter is resilient in a direction perpendicular to the extrusion path, wherein the resilient adapter is a continuous annular rim around the container, and wherein the resilient adapter comprises portions having a wall thickness smaller than a minimum wall thickness of the catch so that the resilient adapter is laterally more resilient than the catch, wherein an inner surface of the resilient adapter is spaced from an outer surface of the container.

19. The dispensing device of claim 18, wherein the resilient adapter protrudes further laterally outwardly with respect to the container than the catch.

* * * * *